United States Patent [19]

Euteneuer

[11] Patent Number: 5,053,007
[45] Date of Patent: Oct. 1, 1991

[54] COMPRESSION BALLOON PROTECTOR FOR A BALLOON DILATATION CATHETER AND METHOD OF USE THEREOF

[75] Inventor: Charles L. Euteneuer, Maple Grove, Minn.

[73] Assignee: SciMed Life Systems, Inc., Maple Grove, Minn.

[21] Appl. No.: 450,664

[22] Filed: Dec. 14, 1989

[51] Int. Cl.⁵ .................... A61M 29/00; A61M 29/02
[52] U.S. Cl. ...................... 604/96; 604/103; 606/194
[58] Field of Search .................... 604/96, 103; 606/194

[56] References Cited

U.S. PATENT DOCUMENTS

| | | |
|---|---|---|
| 2,486,056 | 10/1949 | Oclassen . |
| 3,409,016 | 11/1968 | Foley . |
| 3,822,593 | 7/1974 | Oudewaal . |
| 4,248,246 | 2/1981 | Ikeda . |
| 4,275,591 | 6/1981 | Wand . |
| 4,416,267 | 11/1983 | Garren et al. . |
| 4,449,532 | 5/1984 | Storz . |
| 4,573,470 | 3/1986 | Samson et al. . |
| 4,592,744 | 6/1986 | Jagger et al. . |
| 4,636,201 | 1/1987 | Ambrose et al. . |
| 4,681,092 | 7/1987 | Cho et al. ........................... 604/96 |
| 4,762,125 | 8/1988 | Leiman et al. . |
| 4,771,776 | 9/1988 | Powell et al. . |
| 4,846,174 | 7/1989 | Willard et al. ...................... 604/95 |
| 4,846,344 | 7/1989 | Bala . |
| 4,846,801 | 7/1989 | Okuda et al. . |
| 4,921,483 | 5/1990 | Wijay et al. . |
| 4,930,341 | 6/1990 | Euteneuer ........................... 604/97 |

Primary Examiner—Richard J. Apley
Assistant Examiner—Lynne A. Reichard
Attorney, Agent, or Firm—Kinney & Lange

[57] ABSTRACT

An apparatus for protection of a distal balloon on a dilatation catheter includes an inner compressible sleeve which fits longitudinally over the balloon, an outer compressible sleeve which fits over the inner sleeve, and a housing arrangement for deforming the sleeves radially inwardly about the balloon. The housing arrangement includes first and second threadably mated members which have longitudinally aligned throughbores for receiving the catheter and sleeves, but which act, when threaded together, to compress the outer sleeve onto the inner sleeve and the balloon.

34 Claims, 2 Drawing Sheets

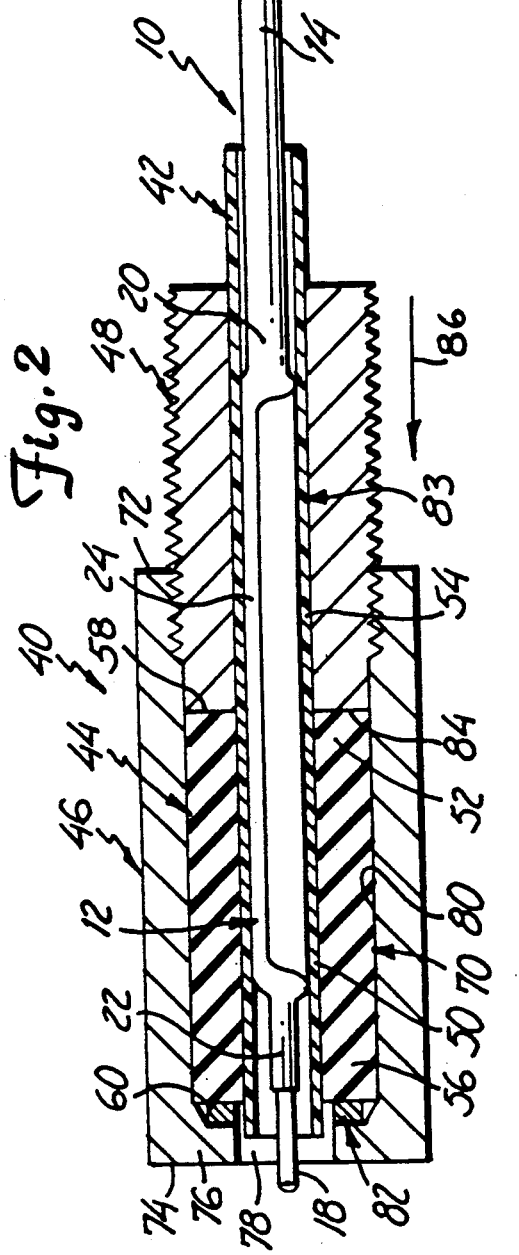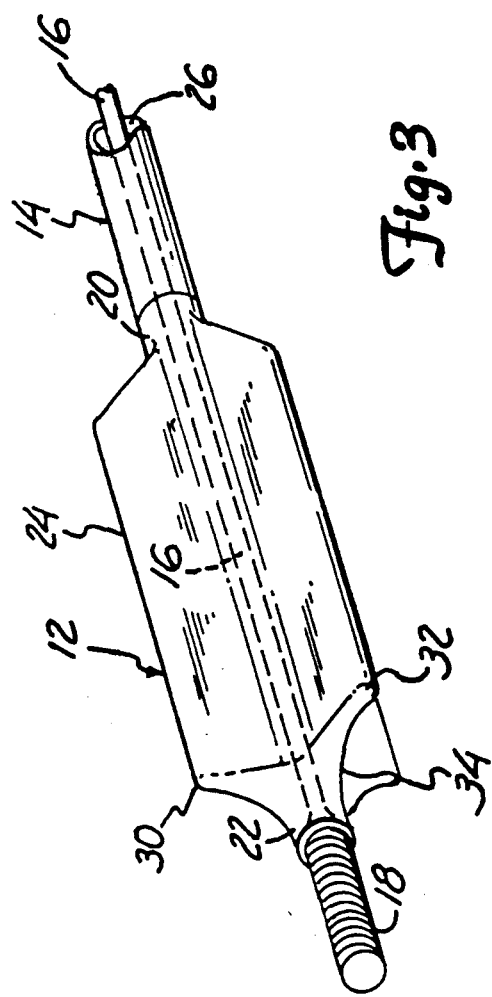

COMPRESSION BALLOON PROTECTOR FOR A BALLOON DILATATION CATHETER AND METHOD OF USE THEREOF

BACKGROUND OF THE INVENTION

1. Field of the Invention

The present invention relates to the field of angioplasty. In particular, the present invention relates to a balloon protector for a dilatation balloon catheter.

2. Description of the Prior Art

Angioplasty is an efficient and effective method for opening stenoses in the coronary arteries and in other parts of the vascular system. The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying a fluid under pressure through an inflation lumen to the balloon. The inflation to the balloon causes stretching of the artery and presses the lesion into the artery wall to re-establish acceptable blood flow through the artery.

An important characteristic of a dilatation balloon catheter used for angioplasty is its "profile" which is determined by the outside diameter of the distal end portion of the balloon. Considerable effort has been spent developing low profile dilatation balloon catheters by minimizing the dimensions of &.he inner tube which extends through the balloon to its distal end, and by reducing wall thickness, to the extent possible, of the balloon itself. Another important consideration is the outer diameter of the balloon in its deflated condition. This outer diameter affects the ease and ability of the dilatation catheter to pass through a guide catheter and through the coronary arteries leading to the stenosis to be opened. In order to reduce the outer diameter of the balloon catheter in its deflated condition, the flaps of the deflated balloon are commonly folded and or wrapped. When inflation fluid is applied to the deflated balloon, the balloon flaps unwrap as the balloon inflates to permit the balloon to assume to its full inflated state.

It has been common to use a balloon protector in conjunction with a balloon dilatation catheter. A balloon protector serves two important functions. First, it protects the balloon and the distal tip of the catheter from possible damage during shipping. Second, the balloon protector wraps the balloon tightly in its deflated condition to minimize the outer diameter of the balloon in its deflated state.

A balloon protector is typically applied to the distal end portion of the catheter prior to sterilization of the catheter. The sterilization process typically involves exposing the catheter, with the balloon protector in place, to an elevated temperature for a predetermined time period.

With certain balloon materials, such as polyolefin, the sterilization process causes the balloon to be "heat set" in the folded or wrapped condition in which it is held by the balloon protector. As a result, when the balloon protector is later removed, the balloon remains in a tightly wrapped condition. This heat set of the balloon has a further advantage in that when the balloon is inflated and is then deflated, the application of a negative fluid pressure during deflation will cause the balloon to tend to return to its heat set tightly wrapped shape. This greatly facilitates the removal of the catheter after the dilatation procedure has been performed.

As the catheter distal sections (including the balloon) have become smaller, and more fragile, it has become increasingly difficult to apply a balloon protector which does not damage the catheter or the balloon and yet wraps the balloon as tightly as possible. There is a continuing need for improved balloon protectors for dilatation balloon catheters.

SUMMARY OF THE INVENTION

The present invention is a compression sleeve balloon protector and method of uninflated balloon compression. The invention employs an inner balloon protector sleeve applied over a deflated balloon, an outer balloon compression sleeve applied over the inner sleeve, and means for urging the outer compression sleeve radially inwardly. The inner balloon protector sleeve is constructed so as to be radially compressible, so that as the outer sleeve is urged radially inward, the inner sleeve is compressed about the balloon.

In one preferred embodiment of the present invention, the inner balloon protector sleeve comprises a tube adapted for receiving at least a distal half of the balloon. The outer balloon sleeve is likewise applied over at least a distal portion of the balloon and inner protector sleeve covering the balloon. A compression housing having a counterbore therein for receiving the outer balloon protector sleeve and the balloon is applied over the outer balloon protector sleeve. A compression member which is movable longitudinally with respect to the counterbore of the housing is threadably received within a proximal end of the counterbore. By tightening the compression member into the counterbore of the housing, the outer balloon protector sleeve compresses onto the inner sleeve, which in turn compresses radially in on the balloon, thereby, setting the profile of the balloon.

With the balloon being compressed by the balloon protector, the catheter is then sterilized at an elevated temperature. The inner and outer sleeves are preferably formed of materials which exhibit heat-shrink characteristics, yet will not adhere to the balloon material. As a result, the heat treatment further causes the deflated balloon to be compressed and therefore have a smaller outer diameter. When a balloon material is used which exhibits heat set characteristics, the deflated balloon will remain tightly compressed even after removal of the outer and inner balloon protector sleeves just prior to use.

BRIEF DESCRIPTION OF DRAWINGS

FIG. 2 is a longitudinal sectional view of the compression balloon protector of the present invention, as assembled on a balloon.

FIG. 3 is a perspective view of a partially inflated balloon, showing the nature of the flaps which are formed in the balloon and which are compressed by means of the present invention.

DETAILED DESCRIPTION OF THE PREFERRED EMBODIMENTS

Figure 1:
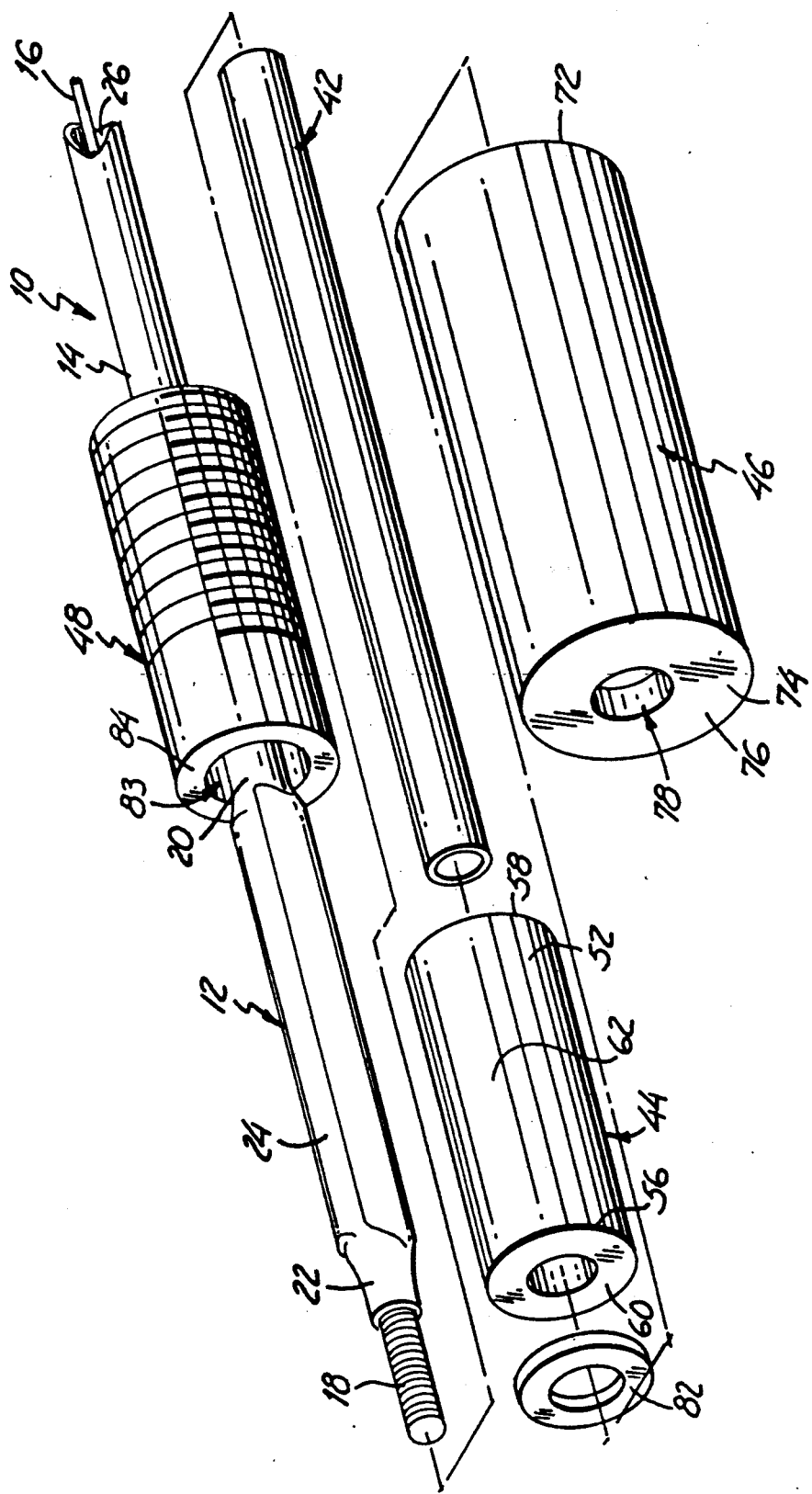
FIG. 1 is an exploded perspective view of the compression balloon protector of the present invention and the distal balloon area of a dilatation catheter.

In FIGS. 2 and 3, a dilatation balloon catheter 10 is shown as a "non-over-the-wire" or "fixed wire" type of balloon catheter having an inflatable balloon 12 mounted at the distal end of a hollow flexible shaft 14. A core member 16 (see FIG. 3) extends through the interior of the balloon 12 and has a spring coil tip 18 at its distal end. The balloon 12 also has a proximal portion 20, a distal portion 22, and an expandable median portion 24 therebetween. The proximal portion 20 of the balloon 12 is bonded to the distal end of the shaft 4, and the distal portion 22 of the balloon 12 is bonded to the core member 16 and/or its coil tip 18. An inflation lumen 26 extends through the interior of the shaft 14 and is in fluid communication with the interior of the balloon 12. The proximal end of the shaft 14, which is not shown, is preferably connected to a manifold, which in turn is connected to an inflation device so that fluid pressure can be applied through the inflation lumen 26 to the interior of the balloon 12. By applying positive fluid pressure, the balloon 12 is inflated. By applying negative fluid pressure (for example, by drawing a vacuum at the proximal end of the lumen 26), the balloon 12 is collapsed to its deflated condition.

The catheter and balloon described herein is merely illustrative. For example, an integral catheter (one-piece balloon and shaft) would work just as well with the present invention. Similarly, an "over-the-wire" balloon catheter can be used with the present invention, although a mandrel or temporary core may be necessary within the balloon during compression to prevent structural collapse of the balloon.

In the particular embodiment illustrated, the balloon 12 has, in its deflated state, three wings or flaps 30, 32 and 34. The use of a balloon having a trifold configuration, while offering significant advantages, is not critical to the balloon protector of the present invention, which is equally applicable to balloons having other deflated shapes and fold arrangements.

The compression balloon protector of the present invention, designated generally by reference numeral 40 in FIG. 2, includes four basic components: an inner balloon protector sleeve 42, an outer balloon protector sleeve 44, and first and second threadably coupled compression housing members 46 and 48. These components are illustrated in FIGS. 1 and 2.

The inner balloon protector sleeve 42 is a compressible tube, preferably open at both ends and having a length approximately equal to the length of balloon 12. The interior diameter of the inner sleeve 42 is slightly larger than the outer diameter of the balloon 12 in its deflated state to permit the balloon 12 to be inserted longitudinally into the interior of the inner sleeve 42, as seen in FIG. 2. The inner sleeve 42 is applied over the balloon 12 by gently moving the inner sleeve 42 proximally from the distal tip 18 of the dilatation balloon catheter until preferably, at least a distal portion 50 of the uninflated balloon 12 (approximately the distal half of the balloon) is covered by the inner sleeve 42.

The outer balloon protector sleeve 44 is an elastic, compressible tubular body, again preferably open at both ends and having a length of approximately one-half the length of the inner sleeve 42. The interior diameter of the outer sleeve 44 is slightly larger than the outer diameter of inner sleeve 42 to permit the inner sleeve 42 to be inserted longitudinally into the interior of the outer sleeve 44, as seen in FIG. 2. The outer sleeve 44 is applied over the balloon catheter 10 in the same manner as the inner sleeve 42, proximally from the distal tip 18 of the balloon catheter 10. As seen in FIG. 2, the outer sleeve 44 is positioned around that part of the inner sleeve 42 which covers the distal portion 50 of the balloon 12. As such, a first proximal end 52 of the outer sleeve 44 is aligned proximal to a median portion 54 of the balloon 12, and a second distal end 46 of the outer sleeve 44 is aligned distally thereof. At its proximal end 52, the outer sleeve has a lateral end surface 58, and its distal end 56, it has a lateral end surface 60. Between its proximal and distal lateral end surfaces 58 and 60, the exterior of the outer sleeve 44 is defined as an outer cylindrical surface 62.

In a preferred embodiment, the inner and outer sleeves 42 and 44 are formed from a heat shrinkable material which also will not stick to the balloon catheter (and particularly to the balloon 12). One preferred material for inner and outer sleeves 42 and 44 is polytetrafluoroethylene.

As illustrated in FIG. 2, the inner sleeve 42 and outer sleeve 44 are received within the first and second threadably coupled compression housing members 46 and 48. The compression housing members 46 and 48 are constructed of generally rigid noncompressible materials, and are adapted to retain the outer sleeve 44 and apply compression forces longitudinally thereon, which urges the outer sleeve 44 radially inwardly about the inner sleeve 42, and further radially inwardly about balloon 12 to compress the balloon.

The first housing member 46 is an outer housing member, which has a longitudinal counterbore 70 therein extending from an open threaded end 72 of the housing member 46 to an opposed, partially closed end 74 thereof. At its closed end 74, the outer housing member 46 has a lateral wall 76, with a central bore 78 therethrough, of diameter larger than the outer diameter of the inner sleeve 42. Counterbore 70 in the outer housing member 48 has a cylindrical inner bore surface 80, and is of a diameter slightly larger than the outer diameter of the outer sleeve 44. Upon assembly, an annular spacer 82 is inserted into the counterbore 70 and positioned between the lateral wall 76 of housing member 46 and the lateral end surface 60 of the outer sleeve 44, as seen in FIG. 2. The outer housing member 46 has a length at least equal to a distal half of the balloon 12, and as assembled, the lateral end surface 60 of the outer sleeve 44 is juxtaposed against an inner surface of wall 76 (with spacer 82 therebetween) of the housing member 46, the outer cylindrical surface 62 of the inner sleeve is juxtaposed against the cylindrical inner bore surface 80 of the counterbore 70 of the outer housing member 46, and at least a distal one-half of the inner sleeve 42 and balloon 12 therein are received in the counterbore 70.

The second housing member 48, is an inner housing member, which is receivable within the counterbore 70 and is threaded to mate with the threaded end 72 of the outer housing member 46 for longitudinal movement relative thereto. The inner housing member 48 has a central longitudinal throughbore 83 therethrough which is aligned with the bore 78 of the outer housing member 46 and which has an inner diameter slightly larger than the outer diameter of the inner sleeve 42. The throughbore 83 in the inner housing member 48 allows it to be moved longitudinally over the inner sleeve 42. The inner housing member 48 has a lateral distal end surface 84 which, upon assembly, is juxtaposed with the proximal lateral end surface 58 of the outer sleeve 44. Movement of the inner housing member 48 into the counterbore 70 (in direction of arrow 86 in FIG. 2) by actuation of the mated threads urges the outer sleeve 44 distally and compresses the outer sleeve 44 longitudinally between the end 74 of the outer housing member and the lateral end surface 84 of the inner housing member 48. Outward expansion of the outer sleeve 44 is prevented by the cylindrical inner bore surface 80 of the counterbore 70. Thus, as deformed, the inner sleeve 44 can only expand radially inwardly against the inner compressible sleeve 42 and further, against the balloon 12. Continued distal movement of inner housing member 48, with respect to outer housing member 46, pushes the juxtaposed surfaces together to deform the outer compression sleeve 44 radially inwardly against the inner compression sleeve 42 and the balloon 12, tightly wrapping the balloon flaps 30, 32 and 34 about the balloon and reducing the deflated outer diameter of the balloon 12 to the desired profile. As seen in FIG. 2, the inner housing member 48 is long enough, upon assembly with the outer housing member 46, that the entire length of the balloon 12 is covered by and thus protected by the compression balloon protector 40.

After the compression balloon protector is in place over the balloon 12, a sterilization heat treatment is performed on the catheter 10. This causes the balloon 12 to be heat-set in its further compressed form. The heat setting of the balloon 12 provides a "memory" to the balloon 12 so that when inner and outer balloon protector sleeves 42 and 44 are removed, the balloon 12 will remain in its tightly wrapped, compressed form.

Prior to use, a balloon catheter is typically inflated to test for leaks and pressure retention. Using the compression balloon protector of the present invention, even after a balloon has been inflated for testing, when it is again deflated for use, it will tend to return to substantially the same shape that it had during the heat sterilization process, with its flaps fully wrapped down for a low profile.

In conclusion, the present invention is an balloon protector arrangement which is effective in creating a tightly-wrapped balloon configuration without tearing or otherwise damaging the balloon and without bending or collapsing the core of the balloon catheter. Using the present invention, the entire length of a balloon can be compressed, although as illustrated, it may be only necessary to tightly compress the distal portion or half of a balloon. This is because only the distal portion of the balloon need pass through the stenosis in order to align the balloon for dilatation of the stenosis.

Although the present invention has been described with reference to preferred embodiments, workers skilled in the art will recognize the changes that may be made in form and detail without departing from the spirit and scope of the invention.

What is claimed is:

1. A balloon protector for a balloon catheter having a balloon positioned adjacent a distal end, the balloon protector comprising:
   an inner compressible tube having an interior for receiving the balloon;
   an outer compression sleeve having an interior for receiving the inner tube; and
   means for urging the outer compression sleeve radially inwardly.

2. The balloon protector of claim 1 wherein the inner compressible tube extends generally longitudinally along the balloon.

3. The balloon protector of claim 2 wherein the inner compressible tube has a length at least equal to a length of the balloon.

4. The balloon protector of claim 1 wherein a distal portion of the inner compressible tube is covered by the outer compression sleeve.

5. The balloon protector of claim 4 wherein the distal portion of the inner tube receives approximately a distal half of the balloon.

6. The balloon protector of claim 1 wherein the inner compressible tube and the outer compression sleeve have holes located at distal ends thereof adapted for receiving a distal tip portion of the balloon catheter.

7. The balloon protector of claim 1 wherein the outer compression sleeve extends generally longitudinally along the balloon.

8. The balloon protector of claim 1 wherein the outer compression sleeve is made of an elastic material.

9. The balloon protector of claim 1 wherein the balloon has a proximal portion, a distal portion and a median portion therebetween, and the outer compression sleeve has a first end located proximal to the median portion of the balloon and a second end located distally thereof.

10. The balloon protector of claim 1 wherein the means for urging the outer compression sleeve radially inwardly includes a compression housing having a counterbore therein for receiving the outer compression sleeve, the inner compressible tube and the balloon.

11. The balloon protector of claim 10 wherein the compression housing has a length at least equal to a distal one-half of the balloon.

12. The balloon protector of claim 10 wherein the outer compression sleeve has a distal lateral end surface and wherein the counterbore of the compression housing is in part defined by a distal lateral wall, and further comprising:
   a spacer positioned between the end surface of the outer compression sleeve and the wall of the counterbore.

13. The balloon protector of claim 10 wherein means for urging the outer compression sleeve radially inwardly further includes a compression member receivable within the counterbore of the compression housing.

14. The balloon protector of claim 13 wherein the compression member has a longitudinal throughbore to receive the inner compressible tube.

15. The balloon protector of claim 13 wherein the compression member is longitudinally movable with respect to the counterbore of the compression housing.

16. The balloon protector of claim 14 wherein a distal end of the compression member is threadably received within a proximal end of the counterbore of the compression housing.

17. The balloon protector of claim 16 wherein the compression member has a distal lateral end surface and the counterbore has a cylindrical inner bore surface and a distal lateral wall, and wherein the compression sleeve has a proximal lateral end surface which juxtaposes the distal lateral end surface of the compression member, a distal lateral end surface which juxtaposes the distal lateral wall of the counterbore and an outer cylindrical sleeve surface which juxtaposes the cylindrical inner bore surface of the counterbore, whereby distal movement of the compression member with respect to the compression housing pushes the juxtaposed surfaces together so that further distal movement of the compression member deforms the compression sleeve radially inwardly against the inner compressible tube and the balloon.

18. A method for forming a balloon protector over a balloon positioned adjacent a distal end of a balloon catheter, the method comprising the steps of:

covering the balloon with an inner compressible tube;

covering at least a distal portion of the inner tube with an outer compression sleeve; and urging the outer compression sleeve radially inwardly.

19. The method of claim 18 wherein the urging step includes the steps of containing the outer compression sleeve in a counterbore; and forcing the outer compression sleeve against the walls of the counterbore to such an extent that the outer compression sleeve deforms radially inwardly against the inner compression tube and the balloon therein.

20. The method of claim 19 and further comprising the steps of:

providing a housing with the counterbore defined therein;

providing a member receivable within the counterbore and movable longitudinally with respect to the housing; and moving the member with respect to the housing to deform the compression sleeve radially inwardly.

21. In combination:

a balloon catheter having a shaft and a balloon attached to the shaft at a distal end of the shaft;

a balloon protector covering the balloon while the balloon is in a deflated state, the balloon protector comprising:

an inner compressible tube covering the balloon;

an outer compression sleeve covering at least that portion of the inner compressible tube over a distal segment of the balloon; and means for urging the outer compression sleeve radially inwardly against the inner compressible tube and the balloon.

22. The combination of claim 21 wherein the inner compressible tube extends generally longitudinally along the balloon and covers a length at least equal to a length of the balloon.

23. The combination of claim 21 wherein the distal segment of the balloon is approximately a distal half of the balloon.

24. The combination of claim 21 wherein the inner compressible tube and the outer compression sleeve have holes located at distal ends thereof adapted for receiving a distal tip portion of the balloon catheter.

25. The combination of claim 21 wherein the outer compression sleeve is made of an elastic material.

26. The combination of claim 21 wherein the balloon has the distal segment, a proximal segment and a median portion therebetween, and the outer compression sleeve has a first end located proximal to the median portion of the balloon and a second end located distally thereof.

27. The combination of claim 21 wherein the means for urging the outer compression sleeve radially inwardly against the inner compressible tube and the balloon includes a compression housing having a counterbore therein holding the outer compression sleeve, the inner compressible tube and the balloon.

28. The combination of claim 27 wherein the compression housing has a length at least equal to the distal segment of the balloon.

29. The combination of claim 27 wherein the outer compression sleeve has a distal lateral end surface and wherein the counterbore of the compression housing is in part defined by a distal lateral wall, and further comprising:

a spacer positioned between the end surface of the outer compression sleeve and the wall of the counterbore.

30. The combination of claim 27 wherein means for urging the outer compression sleeve radially inwardly against the inner compressible tube and the balloon further includes a compression member within the counterbore of the compression housing.

31. The combination of claim 30 wherein the compression member has a longitudinal throughbore holding the inner compressible tube.

32. The combination of claim 30 wherein the compression member is longitudinally movable with respect to the counterbore of the compression housing.

33. The combination of claim 30 wherein a distal end of the compression member is threadably held within a proximal end of the compression housing.

34. The combination of claim 32 wherein the compression member has a distal lateral end surface and the counterbore has a cylindrical inner bore surface and a distal lateral wall, and wherein the compression sleeve has a proximal lateral end surface which juxtaposes the distal lateral end surface of the compression member, a distal lateral end surface which juxtaposes the distal lateral wall of the counterbore and an outer cylindrical sleeve surface which juxtaposes the cylindrical inner bore surface of the counterbore, whereby distal movement of the compression member with respect to the compression housing pushes the juxtaposed surfaces together so that further distal movement of the compression member deforms the compression sleeve radially inwardly against the inner compressible tube and the balloon.

* * * * *